United States Patent
Baynham

(10) Patent No.: US 7,289,849 B2
(45) Date of Patent: Oct. 30, 2007

(54) ATRIAL PACING THERAPY FOR TREATING MITRAL REGURGITATION

(75) Inventor: Tamara Colette Baynham, Blaine, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 77 days.

(21) Appl. No.: 11/046,132

(22) Filed: Jan. 28, 2005

(65) Prior Publication Data

US 2006/0173502 A1 Aug. 3, 2006

(51) Int. Cl.
*A61N 1/00* (2006.01)
*A61B 5/02* (2006.01)

(52) U.S. Cl. .................. 607/9; 607/4; 607/15; 600/528

(58) Field of Classification Search .................. 607/4, 607/9, 15; 600/528
See application file for complete search history.

(56) References Cited

U.S. PATENT DOCUMENTS

| | | | |
|---|---|---|---|
| 6,643,546 B2* | 11/2003 | Mathis et al. | 607/9 |
| 6,795,732 B2* | 9/2004 | Stadler et al. | 607/17 |
| 6,839,592 B2* | 1/2005 | Grandjean | 607/9 |
| 2005/0154422 A1* | 7/2005 | Band et al. | 607/17 |

* cited by examiner

*Primary Examiner*—Carl Layno
*Assistant Examiner*—Natasha Patel
(74) *Attorney, Agent, or Firm*—Schwegman, Lundberg, & Woessner, P.A.

(57) ABSTRACT

A method and apparatus are disclosed for treating mitral regurgitation with electrical stimulation. By providing pacing stimulation to the left atrium during ventricular systole, a beneficial effect is obtained which can prevent or reduce the extent of mitral regurgitation.

14 Claims, 3 Drawing Sheets

ATRIAL PACING THERAPY FOR TREATING MITRAL REGURGITATION

FIELD OF THE INVENTION

This invention pertains to cardiac devices such as pacemakers and other types of devices for treating cardiac dysfunction.

BACKGROUND

The tricuspid and mitral valves, also referred to as the atrioventricular valves, separate the atrium and ventricle on the right and left sides of heart, respectively. The function of the atrioventricular valves is to allow flow of blood between the atrium and ventricle during ventricular diastole and atrial systole but prevent the backflow of blood during ventricular systole. The mitral valve is composed of a fibrous ring called the mitral annulus located between the left atrium and the left ventricle, the anterior and posterior leaflets, the chordae tendineae, and the papillary muscles. The leaflets extend from the mitral annulus and are tethered by the chordae tendineae to the papillary muscles which are attached to the left ventricle. The function of the papillary muscles is to contract during ventricular systole and limit the travel of the valve leaflets back toward the left atrium. If the valve leaflets are allowed to bulge backward into the atrium during ventricular systole, called prolapse, leakage of blood through the valve can result. The structure and operation of the tricuspid valve is similar.

Mitral regurgitation (MR), also referred to as mitral insufficiency or mitral incompetence, is characterized by an abnormal reversal of blood flow from the left ventricle to the left atrium during ventricular systole. This occurs when the leaflets of the mitral valve fail to close properly as the left ventricle contracts, thus allowing retrograde flow of blood back into the left atrium. Tricuspid regurgitation (TR) occurs in a similar manner. MR and TR can be due to a variety of structural causes such as ruptured chordae tendineae, leaflet perforation, or papillary muscle dysfunction. Functional MR and TR may also occur in heart failure patients due to annular dilatation or myocardial dysfunction, both of which may prevent the valve leaflets from coapting properly.

In acute mitral valve regurgitation, the incompetent mitral valve allows part of the ventricular ejection fraction to reflux into the left atrium. Because the atrium and ventricle are not able to immediately dilate, the volume overload of the atrium and ventricle results in elevated left atrial and pulmonary venous pressures and acute pulmonary edema. The reduction in forward stroke volume due to the reflux through the regurgitant valve reduces systemic perfusion, which if extreme enough can lead to cardiogenic shock. In chronic mitral valve regurgitation, on the other hand, the left atrium and ventricle dilate over time in response to the volume overload which acts as a compensatory mechanism for maintaining adequate stroke volume. The left ventricular dilatation, however, may further prevent proper coaptation of the mitral valve leaflets during systolic ejection, leading to progression of the left ventricular dilatation and further volume overload. Patients with compensated MR may thus remain asymptomatic for years despite the presence of severe volume overload, but most people with MR decompensate over the long term and either die or undergo a corrective surgical procedure.

DETAILED DESCRIPTION

The most common method presently available for definitive treatment of MR is surgical intervention involving repair of the mitral valve or replacement with a mechanical or transplanted valve. In order to provide early and appropriate intervention, patients with MR may be identified by clinical examination and/or with specific imaging modalities such as echocardiography. The present disclosure deals with a method and apparatus for treating mitral (or tricuspid) regurgitation with electrical pacing therapy. Pacing therapy applied in this manner may be used to treat MR either in place of or in addition to the conventional surgical options.

Figure 1A:
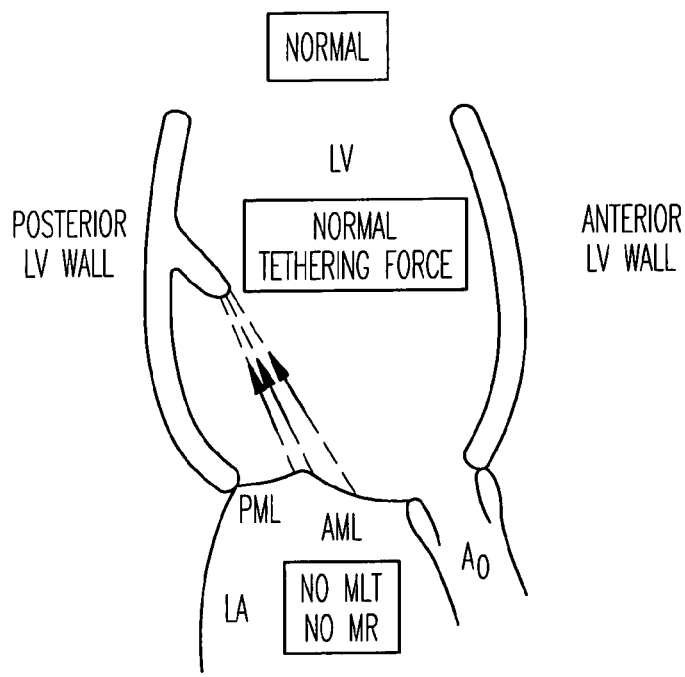
FIGS. 1A and 1B illustrate the mechanisms involved in mitral regurgitation.
Figure 1B:
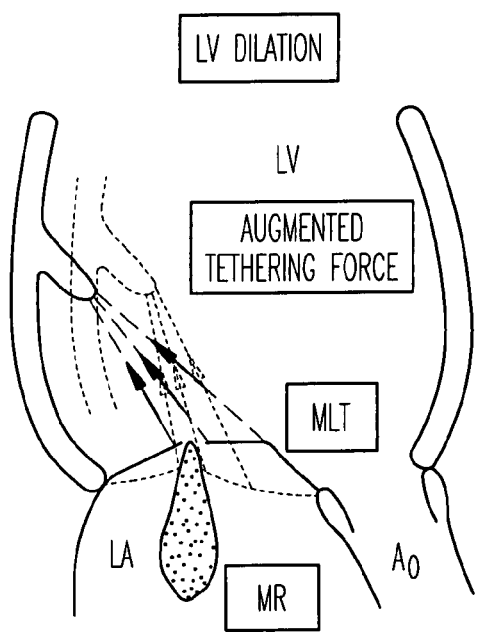

As mentioned above, one mechanism responsible for the development of MR is dilation of the left ventricle which correspondingly dilates the mitral annulus and/or alters its position, thereby preventing proper coaptation of the valve leaflets. Such ventricular dilation occurs in patients suffering heart failure or subsequent to a myocardial infarction as a compensatory response to decreased cardiac output. Heart failure patients may also suffer from electrical conduction deficits which alter the normal activation patterns of the myocardium during systole. Such electrical conduction deficits may result in abnormal timing of papillary muscle contraction which also prevents proper leaflet coaptation. FIGS. 1A and 1B are schematic diagrams of the left ventricle LV, left atrium LA, posterior mitral leaflet PML, anterior mitral leaflet AML, aorta AO, papillary muscle PM, and chordea tendineae CT. FIG. 1A illustrates the normal situation during ventricular systole where the posterior and anterior leaflets are tethered by the chordea tendineae and papillary muscle to the posterior wall of the left ventricle in such a manner that the valve leaflets are coapted, thus preventing reflux flow into the atrium. As the ventricle contracts further, corresponding contraction of the papillary muscle maintains the coaptation of the valve leaflets and prevents them from prolapsing into the atrium. FIG. 1B illustrates the situation where the ventricle is abnormally dilated so as to cause mitral regurgitation. The outward displacement of the ventricular walls and papillary muscle causes an augmented tethering force to be applied to the valve leaflets which prevents proper coaptation and allows reflux flow RF into the atrium. As the ventricle contracts further, simultaneous contraction of the papillary muscle maintains the augmented tethering force and prevents valve closure.

It has been found that atrial pacing therapy may be applied in such a manner that mitral regurgitation is either prevented or lessened in degree in certain patients. In this technique, a pacing electrode is disposed so as to excite the left atrium, e.g., either epicardially or transvenously into the coronary sinus. If the pacing excitation is timed so as to excite the left atrium during ventricular systole, the resulting atrial contraction may cause adequate closure of an otherwise regurgitant mitral valve. One mechanism by which this may come about is the contraction of the region around the mitral valvular annulus during ventricular systole which then constricts the annulus and allows proper coaptation of the valve leaflets to occur. Another mechanism is that the increased atrial pressure during systole augments the tethering force of the papillary muscles and thereby prevents valve prolapse.

The timing of the pacing delivered to left atrium for treating MR should be such that the atrium is excited during ventricular systole. After an atrial contraction at the start of a cardiac cycle, repolarization of the atria normally occurs sometime during ventricular systole, and the atria are refractory to further excitation until this repolarization has taken place. In the presently described technique for treating MR, a left atrial pace is delivered during ventricular systole at a time after a preceding intrinsic or paced atrial contraction sufficient for the left atrium to have recovered from refractoriness. The atrial pace delivered during ventricular systole is referred to herein as a secondary atrial pace as distinguished from a primary atrial pace which, in certain cardiac pacing modes, may be delivered to excite the atrium during atrial systole and before ventricular systole. The timing of the secondary atrial pace may be established with reference to a right or left ventricular sense or pace such that the secondary atrial pace occurs synchronously with a ventricular contraction. A specified delay interval between a ventricular sense or pace and the secondary atrial pace, referred to herein as a secondary ventriculo-atrial (VA) interval, may then be specified so that the left atrium contracts during early ventricular systole. In a patient who is not receiving ventricular pacing therapy, the secondary VA interval is initiated by a ventricular sense. In a patient who is receiving ventricular pacing therapy, the secondary VA interval may be triggered by a ventricular sense or pace.

Alternatively, the timing of the secondary atrial pace may be referenced to an atrial sense and/or to an atrial pace if the patient is also receiving atrial pacing therapy. This may be desirable in certain patients where the optimal timing for the secondary atrial contraction in order to treat MR requires that the left atrium contract before the beginning of electrical ventricular systole as marked by a ventricular sense or pace. In this mode, an atrio-atrio (AA) interval is specified as the delay interval between an atrial sense or pace and delivery of the secondary atrial pace.

Described below is an exemplary device which may be used to deliver secondary atrial pacing therapy to the left and/or right atria. The device is configurable to also deliver conventional bradycardia or resynchronization pacing in addition to the secondary atrial pacing. It should be appreciated, however, that a device for delivering secondary atrial pacing may possess only those features or components necessary for a particular mode of delivery.

1. Exemplary Device Description

Conventional cardiac pacing with implanted pacemakers involves excitatory electrical stimulation of the heart by the delivery of pacing pulses to an electrode in electrical contact with the myocardium. As the term is used herein, a "pacemaker" should be taken to mean any cardiac device, such as an implantable cardioverter/defibrillator, with the capability of delivering pacing stimulation to the heart, including pre-excitation pacing to the mitral valve region as described herein. A pacemaker is usually implanted subcutaneously on the patient's chest, and is connected to electrodes by leads threaded through the vessels of the upper venous system into the heart. An electrode can be incorporated into a sensing channel that generates an electrogram signal representing cardiac electrical activity at the electrode site and/or incorporated into a pacing channel for delivering pacing pulses to the site.

Figure 2:
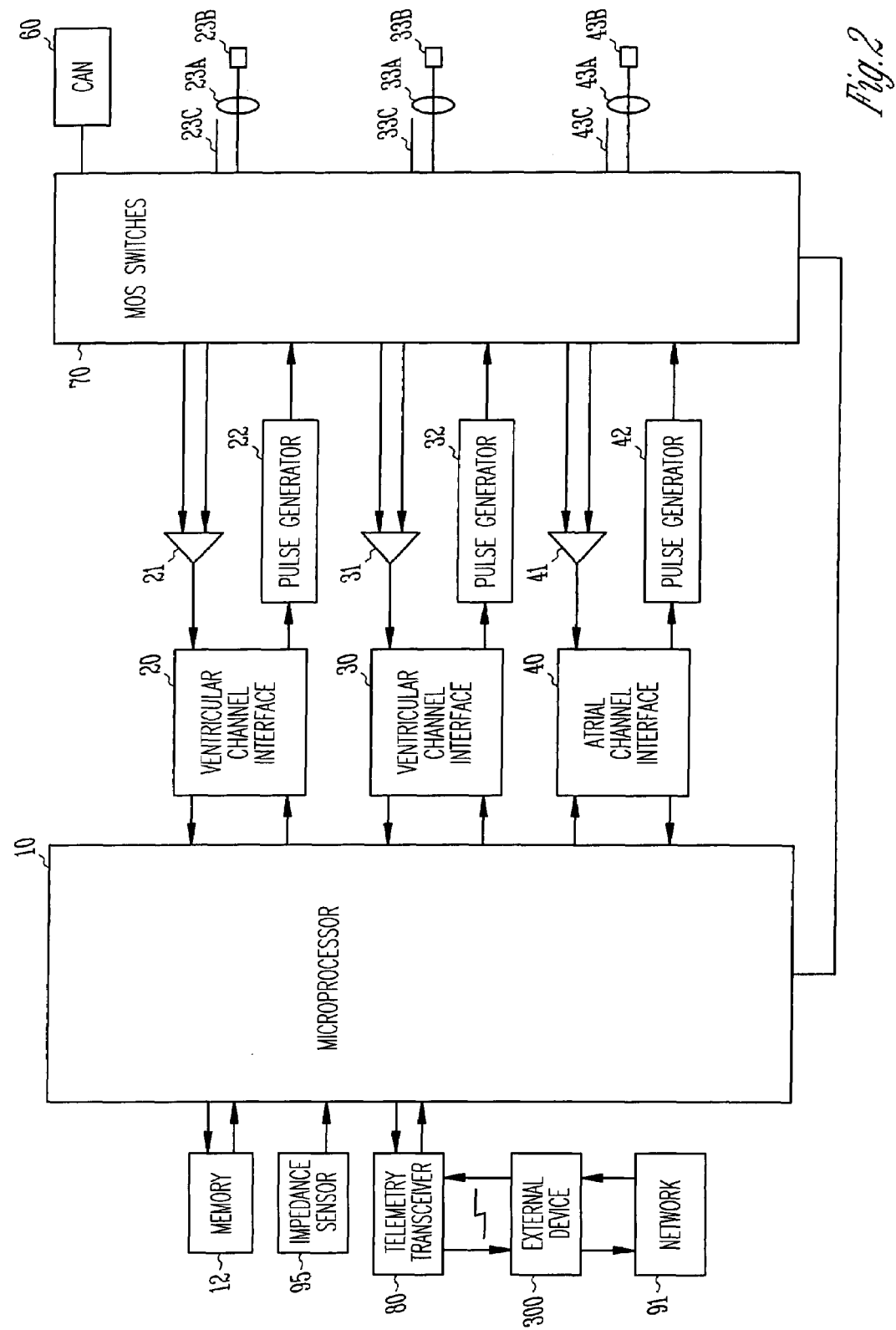
FIG. 2 illustrates an exemplary implantable cardiac device.

A block diagram of an implantable multi-site pacemaker having multiple sensing and pacing channels is shown in FIG. 2. The controller of the pacemaker is made up of a microprocessor 10 communicating with a memory 12 via a bidirectional data bus, where the memory 12 typically comprises a ROM (read-only memory) for program storage and a RAM (random-access memory) for data storage. The controller could be implemented by other types of logic circuitry (e.g., discrete components or programmable logic arrays) using a state machine type of design, but a microprocessor-based system is preferable. As used herein, the programming of a controller should be taken to refer to either discrete logic circuitry configured to perform particular functions or to the code executed by a microprocessor. The controller is capable of operating the pacemaker in a number of programmed modes where a programmed mode defines how pacing pulses are output in response to sensed events and expiration of time intervals. A telemetry transceiver 80 is provided for communicating with an external device such as an external programmer. The external programmer is a computerized device with an associated display and input means that can interrogate the pacemaker and receive stored data as well as directly adjust the operating parameters of the pacemaker. The telemetry transceiver 80 enables the controller to communicate with an external device 300 via a wireless telemetry link. The external device 300 may be an external programmer which can be used to program the implantable device as well as receive data from it or may be a remote monitoring unit. The external device 300 may also be interfaced to a patient management network 91 enabling the implantable device to transmit data and alarm messages to clinical personnel over the network as well as be programmed remotely. The network connection between the external device 300 and the patient management network 91 may be implemented by, for example, an internet connection, over a phone line, or via a cellular wireless link.

The embodiment shown in FIG. 2 has multiple sensing/pacing channels, where a pacing channel is made up of a pulse generator connected to an electrode while a sensing channel is made up of the sense amplifier connected to an electrode. A MOS switching network 70 controlled by the microprocessor is used to switch the electrodes from the input of a sense amplifier to the output of a pulse generator. The switching network 70 also allows the sensing and pacing channels to be configured by the controller with different combinations of the available electrodes. The channels may be configured as either atrial or ventricular channels allowing the device to deliver conventional ventricular single-site pacing, biventricular pacing, or multi-site pacing of a single chamber, where the ventricular pacing is delivered with or without atrial tracking. In an example configuration, three representative sensing/pacing channels are shown. A right atrial sensing/pacing channel includes ring electrode 43a and tip electrode 43b of bipolar lead 43c, sense amplifier 41, pulse generator 42, and a channel interface 40. A right ventricular sensing/pacing channel includes ring electrode 23a and tip electrode 23b of bipolar lead 23c, sense amplifier 21, pulse generator 22, and a channel interface 20, and a left atrial sensing/pacing channel includes ring electrode 33a and tip electrode 33b of bipolar lead 33c, sense amplifier 31, pulse generator 32, and a channel interface 30. The channel interfaces communicate bi-directionally with a port of microprocessor 10 and include analog-to-digital converters for digitizing sensing signal inputs from the sensing amplifiers, registers that can be written to for adjusting the gain and threshold values of the sensing amplifiers, and registers for controlling the output of pacing pulses and/or changing the pacing pulse amplitude. In this embodiment, the device is equipped with bipolar leads that include two electrodes which are used for outputting a pacing pulse and/or sensing intrinsic activity. Other embodiments may employ unipolar leads with single electrodes for sensing and pacing or multi-electrode leads. The switching network 70 may configure a channel for unipolar sensing or pacing by referencing an electrode of a unipolar or bipolar lead with the device housing or can 60.

The controller controls the overall operation of the device in accordance with programmed instructions stored in memory. The controller interprets electrogram signals from the sensing channels, implements timers for specified intervals, and controls the delivery of paces in accordance with a pacing mode. The sensing circuitry of the pacemaker generates atrial and ventricular electrogram signals from the voltages sensed by the electrodes of a particular channel. An electrogram indicates the time course and amplitude of cardiac depolarization and repolarization that occurs during either an intrinsic or paced beat. When an electrogram signal in an atrial or ventricular sensing channel exceeds a specified threshold, the controller detects an atrial or ventricular sense, respectively, which pacing algorithms may employ to trigger or inhibit pacing. An impedance sensor 95 is also interfaced to the controller for measuring transthoracic impedance. The transthoracic impedance measurement may be used to derive either respiratory minute ventilation for rate-adaptive pacing modes or, as described below, cardiac stroke volume for modulating the delivery of secondary atrial pacing.

In order to deliver secondary atrial pacing, one or more pacing channels are configured to secondarily pace the left atrium, each with an electrode disposed near the region to be excited. A sensing channel for the secondarily paced atrial site may or may not also be configured. The controller is then programmed to deliver the secondary left atrial pace during ventricular systole at a specified VA interval subsequent to a ventricular sense or pace or at a specified AA interval subsequent to an atrial sense or pace. The secondary pacing of the left atrium may also be delivered in conjunction with ventricular resynchronization therapy. Ventricular resynchronization therapy is most commonly applied in the treatment of patients with heart failure due to left ventricular dysfunction which is either caused by or contributed to by left ventricular conduction abnormalities. In many such patients, the left ventricle or parts of the left ventricle contract later than normal during systole which thereby impairs pumping efficiency. In order to resynchronize ventricular contractions in these patients, pacing therapy may be applied such that the left ventricle or a portion of the left ventricle is pre-excited relative to when it would become depolarized in an intrinsic contraction. Optimal pre-excitation in a given patient may be obtained with biventricular pacing or with left ventricular-only pacing. In patients who are receiving ventricular resynchronization pacing therapy, the secondary VA interval may be triggered by a sense in either ventricle. The length of the secondary VA interval may be different depending upon which type of event triggered it. For example, if a patient is receiving left ventricular pacing therapy based upon right ventricular senses, a secondary VA interval of one duration may be initiated by a left ventricular pace while a secondary VA interval of another duration is triggered by a right ventricular sense.

2. Exemplary Algorithm

Figure 3A:
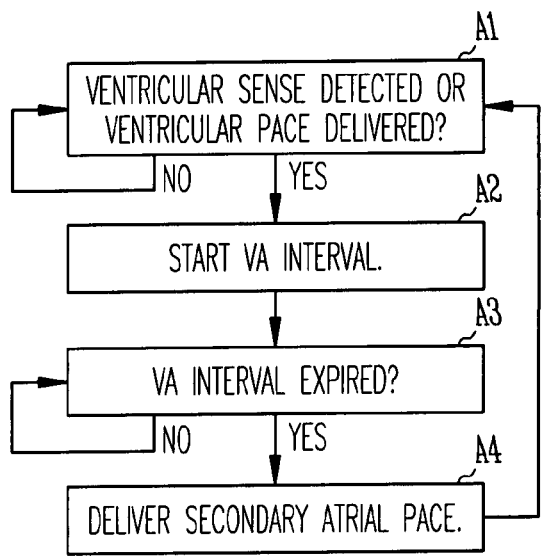
FIGS. 3A and 3B illustrate exemplary algorithms for delivering secondary atrial pacing.
Figure 3B:
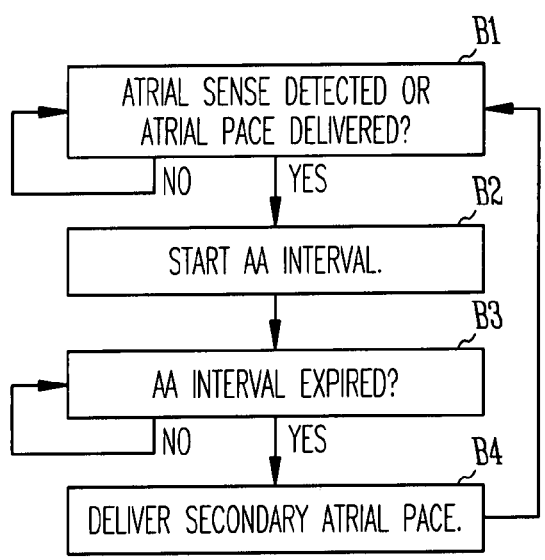

FIGS. 3A and 3B illustrate exemplary pacing algorithms for implementing secondary atrial pacing to treat regurgitant AV valves which may be executed by an appropriately programmed controller. In FIG. 3A, the device waits until a ventricular sense or pace occurs at step A1. After a ventricular sense or pace, a software or hardware timer is started at step A2 which defines the VA interval for delivering the secondary atrial pace. Upon expiration of the VA interval as determined at step A3, the secondary atrial pace is delivered at step A4. FIG. 3B illustrates an embodiment for delivering secondary atrial pacing with timing based upon atrial events. The device waits until an atrial sense or pace occurs at step B1. After an atrial sense or pace, a software or hardware timer is started at step B2 which defines the AA interval for delivering the secondary atrial pace. Upon expiration of the AA interval as determined at step B3, the secondary atrial pace is delivered at step B4.

Clinical testing (e.g., echocardiographic studies) may be employed to determine the optimal time after the beginning of ventricular systole or after an atrial contraction at which secondary atrial pacing should be delivered in order to best treat a patient's MR. In the embodiment of FIG. 3B, the AA interval is optimally set to a value which causes the atrial pace at the appropriate time during ventricular systole. The optimum value of the AA interval therefore depends upon the patient's intrinsic AV interval which varies with heart rate and/or with the programmed paced AV delay interval which may also be programmed to vary with heart rate. In order to compensate for this, the AA interval may also be programmed as a function of measured or paced heart rate by, e.g., using a look-up table or a numerical formula.

A secondary pace delivered so soon after an atrial contraction that the atrium is still refractory will have no effect. It may be desirable, however, to provide a protective period following an atrial sense or pace during which an atrial secondary pace is inhibited in order to prevent pacing an atrium while it is refractory or during a vulnerable period. In the embodiment illustrated by FIG. 3A, this could entail initiating the protective period upon occurrence of an atrial sense or pace. In the embodiment of FIG. 3B, it would amount to simply setting a minimum limit to which the AA interval could be set to.

3. Other Embodiments

It may be desirable in certain patients to control the delivery of secondary left atrial pacing so that such pacing is delivered only when it is needed to lessen mitral regurgitation. One way in which the extent of mitral regurgitation may be monitored by an implantable device is via a transthoracic impedance measurement reflective of cardiac stroke volume. As mitral regurgitation produces volume overloading of both the left atrium and ventricle, such monitoring of stroke volume may be used to modulate the frequency or duration of the secondary left atrial pacing.

The description set forth above has dealt specifically with techniques and apparatus for treating mitral regurgitation with secondary pacing of the left atrium. It should be appreciated that the same techniques could be used to treat either mitral or tricuspid regurgitation with secondary pacing of the right or left atrium depending upon which of the atrio-ventricular valves is regurgitant. If both atrio-ventricular valves are regurgitant, both atria may be secondarily paced with the same or different secondary VA intervals.

Although the invention has been described in conjunction with the foregoing specific embodiments, many alternatives, variations, and modifications will be apparent to those of ordinary skill in the art. Other such alternatives, variations, and modifications are intended to fall within the scope of the following appended claims.

What is claimed is:

1. A method comprising:
   identifying a regurgitant mitral or tricuspid valve in a patient;
   implanting a cardiac rhythm management device in the patient for delivering pacing therapy to the heart through one or more pacing electrodes;
   delivering ventricular pacing therapy and pacing therapy in a manner which excites an atrium during ventricular systole, referred to as secondary atrial pacing;
   delivering the secondary atrial pacing with timing based upon ventricular events such that a secondary atrial pace is delivered at a secondary ventricular-atrio interval subsequent to a ventricular pace or sense; and,
   delivering left ventricular pacing therapy based upon right ventricular senses, wherein a secondary ventricular-atrio interval of one specified duration is initiated by a left ventricular pace while a secondary ventricular-atrio interval of another duration is triggered by a right ventricular sense.

2. The method of claim 1 wherein the ventricular pacing therapy is delivered as biventricular pacing.

3. The method of claim 1 wherein the secondary atrial pacing is delivered at multiple atrial pacing sites.

4. The method of claim 1 further comprising measuring trans-thoracic impedance to derive a measurement reflective of cardiac stroke volume.

5. The method of claim 4 further comprising modulating the frequency of the secondary atrial pacing in accordance with measured cardiac stroke volume.

6. The method of claim 4 further comprising modulating the duration of the secondary atrial pacing in accordance with measured cardiac stroke volume.

7. The method of claim 1 further comprising initiating a protective period following an atrial sense or pace during which an atrial secondary pace is inhibited.

8. The method of claim 1 further comprising providing a trans-thoracic impedance sensor for providing a measurement reflective of cardiac stroke volume.

9. The method of claim 8 further comprising modulating the frequency of the secondary atrial pacing in accordance with measured cardiac stroke volume.

10. The method of claim 8 further comprising modulating the duration of the secondary atrial pacing in accordance with measured cardiac stroke volume.

11. An implantable cardiac device, comprising:
    pulse generating circuitry coupled to one or more electrodes and configured to deliver pacing pulses to a cardiac chamber;
    sensing circuitry coupled to one or more electrodes and configured to detect electrical activity from a cardiac chamber;
    a controller coupled to the pulse generating and sensing circuitry and configured to control the delivery of pacing pulses;
    wherein the controller is programmed to delivering pacing therapy in a manner which excites an atrium during ventricular systole, referred to as secondary atrial pacing;
    wherein the controller is programed to deliver ventricular pacing and to deliver the secondary atrial pacing with timing based upon ventricular events such that a secondary atrial pace is delivered at a secondary ventricular-atrio interval subsequent to a ventricular sense or pace; and,
    wherein the controller is programmed to deliver left ventricular pacing therapy based upon right ventricular senses, wherein a secondary ventricular-atrio interval of one specified duration is initiated by a left ventricular pace while a secondary ventricular-atrio interval of another duration is triggered by a right ventricular sense.

12. The device of claim 11 wherein the ventricular pacing therapy is delivered as biventricular pacing.

13. The device of claim 11 wherein the controller is programmed to deliver the secondary atrial pacing at multiple atrial pacing sites.

14. The device of claim 11 wherein the controller is programmed to initiate a protective period following an atrial sense or pace during which an atrial secondary pace is inhibited.

* * * * *

UNITED STATES PATENT AND TRADEMARK OFFICE
CERTIFICATE OF CORRECTION

| | | |
|---|---|---|
| PATENT NO. | : 7,289,849 B2 | Page 1 of 1 |
| APPLICATION NO. | : 11/046132 | |
| DATED | : October 30, 2007 | |
| INVENTOR(S) | : Baynham | |

It is certified that error appears in the above-identified patent and that said Letters Patent is hereby corrected as shown below:

In column 8, line 19, in Claim 11, delete "programed" and insert -- programmed --, therefor.

Signed and Sealed this

Twenty Second Day of April, 2008

JON W. DUDAS
*Director of the United States Patent and Trademark Office*